United States Patent

Weigel

[11] Patent Number: 5,563,035
[45] Date of Patent: Oct. 8, 1996

[54] ESTROGEN RECEPTOR REGULATION AND ITS USES

[75] Inventor: Ronald J. Weigel, Woodside, Calif.

[73] Assignee: The Board of Trustees of The Leland Stanford Junior University, Stanford, Calif.

[21] Appl. No.: 260,549

[22] Filed: Jun. 16, 1994

[51] Int. Cl.⁶ .............................. C12Q 1/68; G01N 33/53
[52] U.S. Cl. .................................................. 435/6; 435/7.1
[58] Field of Search .......................................... 435/6, 7.1

[56] References Cited

PUBLICATIONS

Weigel et al, Cancer Research (1993); vol. 53: pp. 3472–3474.
Hakim, "Prognostic Significance of mRNA–Encoding Estrogen Receptor and Epithelial Growth Factor Receptor in Breast Carcinoma Progression into Lymph Nodes: 1. Estrogen Receptor Encoding mRNA," J. Surg. Oncology (1989) 40:21–31.

*Primary Examiner*—Mindy Fleisher
*Assistant Examiner*—Terry A. McKelvey
*Attorney, Agent, or Firm*—Bertram I. Rowland

[57] ABSTRACT

ERF-1 is shown to be a transcriptional regulator of the expression of the estrogen receptor, where elevated ERF-1 is related to elevated expression of the estrogen receptor. By monitoring the level of ERF-1, one can relate phenotypic characteristics of carcinomas expressing ERF-1 as prognostic of the response of the tumor to various therapies. In addition, ERF-1 may be used for screening therapeutic drugs which may act as antagonists to initiation of estrogen receptor transcription.

8 Claims, No Drawings

ESTROGEN RECEPTOR REGULATION AND ITS USES

Research in support of the inventions claimed in this application was funded in part by American Cancer Society Grant No. IG-RL32-34 and NIH Grant 1R29CA63251-01. The U.S. government may have rights in this application.

INTRODUCTION

1. Technical Field

The field of this invention is breast cancer and endometrial cancer diagnosis and treatment.

2. Background

The expression of estrogen receptor (ER) is intimately associated with the biology of breast carcinoma. Breast carcinomas occurring in postmenopausal women are often ER-positive and many of these tumors express significantly more receptor than normal mammary epithelium. By contrast, ER-negative breast carcinomas are more likely to occur in young women and these tumors carry a worse prognosis than carcinomas which express ER. Several studies have focused on the function of ER in an attempt to explain the association between ER expression and tumor biology. Mutations have been described in the ER gene of some breast carcinomas that render these altered ER proteins incapable of binding estrogen response element (ERE) and able to inhibit wild-type ER function. Other studies, however, have found ER mutations which result in a constitutively active receptor which has also been postulated as important to the development of hormone-independent growth. If ER function is influencing the oncogenic process, it is difficult to conceptualize within a single model of oncogenesis the occurrence of mutations which inhibit ER function and mutations which result in constitutive activity. An alternative hypothesis is that mechanisms regulating transcription of the ER gene influence the phenotype of breast carcinoma; within this model, ER-negative cells which do not transcribe the ER gene define a subset of tumors with a more aggressive phenotype. This theory is supported by recent studies which have identified breast carcinoma cell lines that fail to transcribe an apparently normal ER gene. Defining molecular mechanisms controlling transcription of the ER gene offers opportunities into a broader understanding of the biology of breast carcinoma.

Transcription of ER occurs from two separate promoters, P0 and P1, although no functional mapping has been previously published. P1 represents the major ER transcriptional start site. The P1 cap site is predominantly utilized in human mammary epithelial cells (HMEC) and is the major start site in ER-positive human breast carcinomas. Multiple cap sites have been identified for the P0 promoter. Studies of the murine ER gene identified 10 cap sites spanning approximately 60 bases and a start site at −1994 (from the P1 cap site) was identified in human cells which would agree closely with the major murine P0 cap site. Transcription from the P0 promoter is characteristic of human endometrial tissue and can account for 12 to 33% of ER transcription in breast carcinoma cells.

There is, therefore, substantial interest in being able to identify the role that ER plays in carcinomas. In this manner, one may have a more accurate prognosis of the disease outcome, one may accurately follow therapies, and one may provide for opportunities for varying the aggressiveness of the therapy.

Relevant Literature

Investigation of the role of the estrogen receptor in carcinomas is described by Watts et al., *J. Steroid Biochem. Molec. Biol.* 41(3), 529 (1992); Scott et al., *J. Clinic. Invest.* 88, 700 (1991); Ince et al., *J. Bio. Chem.* 268, 14026 (1993); Fuqua et al., *Can. Res.* 52, 43 (1992); McGuire et al., *Mol. Endocr.* 5, 1571 (1991); Castles et al., *Can. Res.* 53, 5934 (1993); and Weigel and deConinck, *Can. Res.* 53, 3472 (1993). Description of the estrogen receptor mRNA may be found in Keaveney et al., *J. Mol. Endocr.* 6, 111 (1991); Green et al., *Nature* 320, 134 (1986); White et al., *Mol. Endocr.* 1, 735 (1987); and Piva et al., *J. Steroid Biochem. Molec. Biol.* 46, 531 (1993).

SUMMARY OF THE INVENTION

Mammary and endometrial tumors are screened for expression of estrogen receptor factor-1 (ERF-1). For screening, one may use the DNA sequence to which ERF-1 binds, antibodies to the protein, or probes for the messenger RNA. Detection of expression of ERF-1 can be related to the prognosis for the carcinomas. In addition, ERF-1 can be used to identify genes under the transcriptional control of ERF-1 and expression constructs can be prepared, where expression of ERF-1 can initiate transcription of a target gene. The ER transcriptional initiation region including elements affecting transcription initiation (transcriptional initiation related elements—TIRE) can be used as cell-specific initiation elements for investigation of pathways of mammary cells, gene therapy, or the like, using the intact transcriptional inflation region or one or more TIREs in conjunction with TIREs from other genes to provide chimeric initiation regions in which ERF-1 provides for cell-specific expression.

DESCRIPTION OF SPECIFIC EMBODIMENTS

Compositions and methods are provided for screening neoplastic cells for prognosis of outcome, monitoring treatment of the neoplasia, and identifying agents for treatment of the neoplasia, where the normal cells from which the neoplastic cells are derived express estrogen receptor. Particularly, the cells are mammary epithelia and endometrial cells, which can result in carcinomas which may be estrogen dependent or independent. The compositions which find use include the protein, estrogen receptor factor-1 (ERF-1), the coding sequence for ERF-1, and the DNA sequence or enhancer sequence to which ERF-1 binds. It is found that ERF-1 is expressed in normal cells which express estrogen receptor (ER) in ER-positive breast carcinomas, and in ER-positive endometrial carcinomas. Expression of ERF-1 is related to ER regulation in hormonally responsive carcinomas.

The expression of ERF-1 in neoplastic cells may be monitored to determine the prognosis associated with breast and endometrial cancer. ER expression defines a subset of breast cancer patients who, in general, have a better prognosis compared to patients with ER-negative tumors. Expression of ERF-1 may therefore be related to the prognosis associated with ER expression and may serve as a screening tool for therapeutic drugs or regimens for the treatment of mammary and endometrial carcinomas, particularly in the case of ER-negative tumors. Also, the expression of the ERF-1 may be used to monitor the course of treatment to determine whether after treatment the status of expression of ERF-1 has changed.

ERF-1 is characterized by being expressed in estrogen receptor positive cells, binding to a sequence upstream of the coding sequence for the estrogen receptor, binding specifically to the sequence CCCTGCGGGG (SEQ ID NO:01), which is in the sequence +182 to +201 of the estrogen receptor promoter region counting from the cap site of the P1 promoter as +1, with plus being in the direction of the coding region. ERF-1 may be further characterized by being present in ER-positive cells, binding to the sequence +182 to +201 of the ER untranslated leader of the ER mRNA, being of about 29–30 kD, as determined by gel electrophoresis, and being associated with expression of ER in cells, where the expression of ERF-1 is associated with elevated expression of ER.

ERF-1 may be isolated and purified in accordance with conventional ways. See, for example, *Molecular Cloning: A Laboratory Manual*, Sambrook et al., Cold Spring Harbor Laboratory, Cold Spring Harbor, N.Y., 1989. ERF-1 may be cloned by screening a cDNA expression library prepared from ER-positive breast carcinoma cells using a concatenated ERF-1 binding site as a probe. The clones expressing ERF-1 may then be selected for the level of expression of ERF-1 and used for the preparation of ERF-1 in accordance with conventional ways. ERF-1 may then be purified by preparing a lysate from an ERF-1 overproducing cell line, which may be passed through an affinity column comprising DNA sequence, as described above, bound to particles in the affinity column. After washing the column free of non-specifically bound proteins, the specifically bound protein may then be eluted using salt media, which release the protein from the column. The protein may then be freed of the salt using dialysis, and isolated in substantially pure form, generally at least about 50% pure, based on total protein, preferably at least about 75% pure, based on total protein. The protein may then be subjected to a second affinity purification to enhance the ERF-1 purity to at least about 90%. The protein may then be further purified using HPLC.

To obtain the gene product, the purified protein may be sequenced and probes of at least 18 nucleotides designed, which are redundant for one or more sequences coding for the ERF-1 protein. A cDNA library may then be screened with the probes for cDNAs which hybridize to one or more of the probe compositions. The cDNAs may then be isolated and sequenced to determine whether they code for the ERF-1 protein. In this manner, the cDNA encoding the ERF-1 protein may be isolated. The cDNA sequence is then used to identify the genomic sequence by employing a genomic library and identifying hybridizing fragments in the same way as used for identifying the cDNAs originally. Genomic fragments which bind to the cDNAs may then be isolated and introduced into an appropriate mammalian host capable of transcription and translation of the genomic gene, but having an ERF-1 negative or low background. Thus, various cell lines which are deficient in expression of ERF-1 may be employed, where the cell lines exist naturally or as a result of knockout by homologous recombination using the cDNA gene as flanking regions for a marker, such as antibiotic resistance.

The ERF-1 protein may be used to produce antibodies in accordance with conventional ways. The partially or completely purified protein may be used as an immunogen to immunize an appropriate laboratory animal, e.g. mouse, to provide for antisera. See, *Antibodies: A Laboratory Manual*, Harlow and Lane eds., Cold Spring Harbor Laboratory, Cold Spring Harbor, N.Y., 1988. The antisera may be isolated as appropriate, or preferably the spleen is isolated and the splenocytes fused with an appropriate immortalizing biological, e.g. mouse myeloid cells, to provide hybridomas. The hybridomas may be screened in accordance with conventional ways to identify monoclonal antibodies which bind specifically to ERF-1. The hybridomas may then be used for purifying ERF-1 or in diagnostic assays for ERF-1.

The protein ERF-1, fragments thereof, the DNA sequences encoding ERF-1, fragments thereof, and the enhancer sequence associated with the expression of ER may all be used for detecting expression of ERF-1 in a cell, particularly in neoplastic cells associated with normal cells that express the estrogen receptor. The presence of ERF-1 may be determined qualitatively or quantitatively, depending upon the purpose of the diagnosis. It is found that the prognosis for ER positive carcinomas is better in most cases than the prognosis for ER negative carcinomas. However, this comparison has been based on assays which determine the presence of a functional estrogen receptor and do not detect non-functional estrogen receptors, which do not bind estrogen. Such "non-functional" estrogen receptors can still function so far as initiating signals associated with estrogen receptor activation. Detecting the presence and level of ERF-1 expression can be correlated with the expression of the estrogen receptor and mutant forms thereof, so as to provide a better correlation between the expression of estrogen receptor (including mutant forms) and the prognosis. Therefore, the ER minus carcinomas may be further screened for the expression of ERF-1 to define a subset of mammary carcinomas that express a non-functional ER. Based on the prognosis, the nature of the treatment will vary, as to the modality, aggressiveness, drugs employed, extent of the treatment, and the like.

dsDNA sequences of at least 10 nt, usually of at least 12 nt and not more than about 200 nt, usually not more than about 100 nt, of the ER TIRE sequence can be used as probes. The sequence may be labeled terminally, internally or both. Labels may usefully include radioisotopes, biotin, particles, solid surfaces, ligands, e.g. digitalis compounds, such as digoxigenin, fluorescers, e.g. fluorescein, rhodamine, etc., or enzymes, where the label may be covalently bonded to the DNA or bound through a specific binding pair, e.g. biotin and streptavidin. The specific DNA sequence may be extended with further nucleotides, where the flanking region may be used for hybridizing to another sequence, e.g. a sequence bound to a solid surface, for binding the ERF-1 to a surface. In this way, the ERF-1 may be both isolated and quantified.

In assays employing the ERF-1 binding sequence, cells may be lysed and total cell protein isolated in accordance with conventional ways. Cell pellets are suspended in a microextraction buffer, sonicated, and cellular debris pelleted. The concentration of protein may then be determined. Aliquots of the protein may then be combined with radiolabeled sequence in an appropriate binding buffer. The complex may then be purified using gel electrophoresis or other separation technique, which separates the various proteins, one from another, as well as the labeled DNA sequence. Where the DNA sequence is radiolabeled, a densitometer may be used to determine the amount of the complex. Where other labels are used, e.g. biotin, the protein complex may be eluted from the gel and the DNA assayed by binding the protein DNA complex to a solid surface, adding labeled streptavidin, where the label is conveniently a fluorescer or enzyme, and then determining the amount of fluorescence or detectable enzyme product, as a measure of the amount of ERF-1.

With antibodies, one can prepare an appropriate protein lysate and bind the protein to a convenient surface. Labeled antibodies, e.g. fluorescer or enzyme labels, may then be used for binding to protein on the surface. After contacting the protein with the labeled antibody, non-specifically bound antibodies may be washed away, and the amount of bound antibody determined in relation to the particular label.

In addition, ERF-1 antibody can be used to stain slides prepared from cell blocks and ERF-1 can be detected as measured by the presence of the ERF-1 antibody specifically bound to the cells in the cell block. As an example, conventional fluorescence tagged or radioisotope tagged second antibody can be used to measure the presence of the ERF-1 antibody or the ERF-1 antibody may be directly tagged with a detectable label..

Alternatively, one may use the coding sequence of ERF-1 to determine the level of messenger RNA present in the cell. By lysing cells obtained by a biopsy, under conditions which inhibit RNases in accordance with conventional ways, the mRNA may be transcribed into DNA and the DNA expanded using PCR. The expanded DNA may then be quantitated, if desired. Less conveniently, a Northern analysis may be used. The mRNA may be bound to a solid substrate surface. Labeled probes comprising the coding sequence may then be added to the surface under hybridization conditions, under the appropriate stringency. Again, by means of the label, one can determine the level of messenger for ERF-1, using detection of other messenger as a standard in the cells.

By employing any of the above diagnostic techniques, the presence and amount of transcription and expression of ERF-1 may be determined, as a measure of the expression of ER, as well as other proteins whose transcription are regulated by ERF-1. This information is related to the aggressive nature of a particular cancer, the change in the nature of the cancer in relation to treatments, such as irradiation, chemotherapy, or surgery, the metastatic nature of the cancer, as well as the aggressiveness of metastases, and the like. This relationship may be used for determining the level of therapeutic treatment, monitoring the response of the tumor to the therapeutic treatment, and in providing a prognosis for the patient concerning the course of the disease.

The availability of ERF-1 and the DNA sequence to which ERF-1 binds offers many opportunities to screen agents for their potential in the treatment of tumors associated with ER response. ERF-1 may be used for binding affinity studies to determine the binding affinity of various compounds. By providing for competition between labeled DNA binding sequence and the candidate agent, one can measure the amount of unbound sequence as a measure of the affinity of the candidate agent.

One may also use the DNA binding sequence as a decoy, to compete with the ER enhancer for ERF-1. By modifying the DNA to substantially enhance its stability in the presence of DNases, the sequences may bind to ERF-1, inhibiting the expression of ER. The sequences will usually be at least about 12 nt and not more than about 60 nt. The sequence may be modified by substituting oxygen atoms of the phosphate with sulfur, amino, methylene, etc., replace the phosphate esters with peptides, or the like. There is an ample literature describing methods of preparing the modified sequences and screening them for affinity to ERF-1.

The gene for ERF-1 may be used in gene therapy, where an expression cassette may be employed having the wild-type promoter (includes enhancer) or a substitute promoter, where the promoter may be inducible or constitutive. Various promoters functional in mammalian host cells are known such as viral promoters, e.g. SV40, adenovirus, etc., cellular promoters, e.g.β-actin, metallothionein I or II, etc. Alternatively, the gene may be used in investigating the physiology of mammary cancer, by introducing the gene into mammary tumor cells, and determining the effect of varying ERF-1 expression on proliferation, response to therapeutic agents, aggressiveness, metastatic activity and the like. By introducing the tumor into an animal model, e.g. SCID-hu, one may determine the metastatic potential and aggressiveness of the tumor in relation to the level of ERF-1 expression.

The transcriptional initiation region of the estrogen receptor can be used in a variety of ways associated with cell-type specific expression in mammary and endometrial cells. One may use the transcriptional initiation region of ER (includes the leader sequence of the ER mRNA portion to which ERF-1 binds) to provide for cell-type specific transcription and, as appropriate, expression. Thus, this region may be joined to any sequence of interest, such as antisense sequences, to block a specific protein from being expressed. In this way, one may determine the role of a particular gene in the activity of the cell, determine the pathway in which the gene acts, and the like. Alternatively, one may provide for expression of a protein, which may serve as a marker to indicate when ERF-1 is being expressed at a sufficient level to initiate transcription, to modify the phenotype of the cell, or the like.

The region in the leader sequence to which ERF-1 binds can be used with other sequences which bind RNA polymerase to form a chimeric transcriptional initiation region to control expression with the expression of ERF-1. In cells which normally express ERF-1, the chimeric transcriptional initiation region would serve to initiate expression with the expression of ERF-1. In cells which do not express ERF-1, one could introduce an expression cassette which provided for constitutive or inducible expression of ERF-1, so that a gene under the transcriptional control of the chimeric transcriptional initiation region would be expressed. In this manner one provides for expression of a gene by controlling the expression of a transcription factor, ERF-1, which is exogenous to the cell. One can provide for the simultaneous expression of a plurality of cells by controlling the expression of ERF-1, where each of the genes are regulated by the regulatory region of the ER to which ERF-1 binds.

The ability to provide for cell-type specific expression allows for the use of the subject sequences for gene therapy. By using known viral vectors for transfection, one can introduce expression cassette constructs into cells, where the expression cassette becomes integrated and the gene is expressed. Since for a substantial portion of the population which suffers from mammary cancer, there is a diminished number of normal mammary cells, it would not be detrimental if there was transfection of some proportion of the normal cells. In the case of cancer cells, the expressed gene could be a toxin, such as diphtheria toxin, ricin or abrin, an oncogene inhibitor, a surface membrane protein to serve as a specific target for a cytotoxic agent, a chemoattractant or cytokine for attraction of cytotoxic T lymphocytes, combinations thereof, or the like.

The following examples are offered by way of illustration and not by way of limitation.

EXPERIMENTAL

A human genomic lambda library was screened with a probe from the 5' flanking region of the ER gene (Keaveney et al., 1991, supra; Green, et al., 1986, supra). A genomic clone was obtained which contained 3.5 kbp upstream of the P1 cap site for ER, the entire first coding axon, and approximately 10 kbp of the first intron. This 5' flanking region encompasses 500 bp upstream of the farthest ER cap site identified. Regions of this clone were then subcloned into the luciferase reporter vector (pGL2-Basic). The major ER mRNA beginning at P1 contains a 230 base untranslated 5' leader sequence (Green et al., Nature 320, 134 (1986)). In the first set of constructs, all inserts contained 210 bp of the untranslated leader and a nested set of 5' deletions were generated from 3.5 kbp down to the P1 cap site at +1. In a second set of promoter constructs, the 5' end remained at 3.5 kbp and 3' deletions were constructed beginning at +30 and progressively deleting portions of the leader by sequentially bringing the luciferase gene closer to the P1 cap site.

These constructs were tested for luciferase expression upon transfection to breast carcinoma cell lines. T47D is an ER-positive breast carcinoma line in which approximately 90% of the ER mRNA begins at the P1 cap site. The ER-negative carcinoma line, MDA-MB-231 was also used, as this cell line lacks transcription of the ER gene (Weigel and deConinck, Can. Res. 53, 3472 (1993). The following table indicates the result.

TABLE 1

| Plasmid | T47D | MDA-MB-231 |
| --- | --- | --- |
| ER3500-210LUC | 39,009 | 4,362 |
| ER700-210LUC | 0.66 | 1.42 |
| ER550-210LUC | 0.46 | 1.02 |
| ER436-210LUC | 0.86 | 2.69 |
| ER350-210LUC | 0.69 | 2.99 |
| ER260-210LUC | 1.11 | 4.6 |
| ER128-210LUC | 0.73 | 3.17 |
| ER40-210LUC | 0.67 | 3.69 |
| ER0-210LUC | 0.33 | 3.10 |
| pGL2-Basic | 0.03 | 0.32 |
| ER3500-230LUC | 45,482 | 4,245 |
| ER3500-210LUC | 1.08 | 1.13 |
| ER3500-135LUC | 0.22 | 1.16 |
| ER3500-0LUC | 0.06 | 0.18 |
| pGL2-Basic | 0.02 | 0.41 |
| ER3500-230p1d1 | 0.29 | 0.45 |

Legend: Plasmids were constructed with variable amounts of upstream (top) or downstream (bottom) ER gene sequences cloned into the BglII-HindIII site of the luciferase expression vector pGL2-Basic (Promega, Madison, WI). The region of DNA in the 5' end of the ER gene was isolated from a human genomic lambda library (Stratagene, La Jolla, CA). The 5' region was sequenced and a set of primers were constructed, all of which contained a BglII site for use as upstream Primers. All 3' oligonucleotides contain a HindIII site. These oligonucleotide primers were used in polymerase chain reaction with cloned DNA as template. PCR products were then cloned into the BglII-HindIII sites of the reporter plasmid pGL2-Basic. Plasmids were introduced into T47D or MDA-MB-231 cells using calcium phosphate transfection (Graham and VanderEb, Virology 52, 456 (1973)). 30 µg of cloned plasmid DNA was used in transfections of 100 mm plates with cells at 50–60% confluence. In each transfection, 2 µg of an RSV-driven CAT expression vector was cotransfected and cells were assayed for luciferase and CAT expression 48 h after transfection. The values presented are luciferase units as measured on a luminometer corrected for transfection efficiency. Similar results were obtained when 15 µg of plasma DNA was used in transfections. Values shown for the largest construct are luciferase activity corrected for transfection efficiency. Values for smaller constructs are shown as a fraction of the largest construct value. Data for 5' mutations (top) is average value for four separate transfecfion experiments. Data for 3' mutations (bottom) is average for eight separate transfections. For the 5' mutations, the numbers indicate the retained nucleotides 5' of the cap site, which is called 0. For the 3' mutations, the numbers indicate the portion of the region between +1 and +230 downstrream from the cap site, which is deleted, that is the portion of the leader sequence of the mRNA. The data for ER3500-230p1d1 is average for two separate transfections performed in triplicate and is representative of other transfections performed.

The luciferase activity in the T47D and MDA-MB-231 was strikingly different. In the ER-positive T47D, the full-length construct gave excellent expression. Progressive deletion of the 5' end of the gene failed to significantly alter expression, although there was a reproducible decline of expression upon deletion of the last 40 bp of the 5' flanking region which contains a TATA element at +25.

The pattern of expression in ER-negative MDA-MB-231 was qualitatively and quantitatively different. The full-length construct expressed poorly and gave values an order of magnitude less than in T47D. This level of expression was only three times the expression from the negative control vector pGL2-Basic, which does not contain a promoter. Progressive deletion of the upstream sequences improved expression and no significant decline occurred when the TATA element upstream of the P1 cap site was deleted. Deletions from the 3' end of the leader identified a sequence between +210 and +135 which augments expression of the ER promoter in ER-positive T47D cells. Analysis of these constructs in ER-negative MDA-MB-231 was also performed and the effect of this region appeared to be cell line specific.

Protein binding to this region of the ER gene was discovered as follows. An 80 bp probe was prepared from sequences from +132 to +211 of the ER promoter. This probe was used in gel-shift assays with extracts prepared from the ER-positive breast carcinoma cell lines (MCF7 and T47D) and the ER-negative MDA-MB-231 cell line. The gel shift assay was performed using whole cell extracts. Cell pellets were washed with 1× PBS and cells were resuspended at $10^8$ cells/ml in microextraction buffer [450 mM NaCl, 20 mM HEPES, pH 7.7, 25% glycerol, 0.2 mM EDTA, 0.5 mM DTT, and proteinase inhibitors]. Cells were sonicated and cellular debris was pelleted at 14,000 rpm in a microfuge. Protein concentration of the supernatant was determined using a Bio-Rad protein assay (Hercules, Calif.) and ran in the range of 5–15 mg/ml. Extracts were stored at −80° C. until use. 10 µg of total cell protein was incubated in 1×binding buffer [40 mM KCl, 20 mM HEPES, pH 7.7, 1 mM $MgCl_2$, 0.1 mM EDTA, 0.4 mM DTT], 4% Ficoll, 40 µg/ml poly dI-dC, 0.1 ng of radiolabeled probe in a volume of 25 µl at room temperature for 45 min. Reactions were then loaded on 4% PAGE in 0.25× TBE and electrophoresed at 270 volts at 4° C. Gels were then dried and exposed to x-ray film.

Double stranded DNA oligonucleotides were prepared by separately synthesizing each strand of the oligonucleotide using a Gene Assembler Special (Pharmacia LKB, Alameda, Calif.). Oligonucleotides were mixed in equimolar ratio in 0.3M sodium acetate, boiled for 10 min and cooled slowly to room temperature. Double stranded DNA was then ethanol precipitated and resuspended in water at a concentration of 0.2 mg/ml.

A prominent shift band was found only in extracts from the ER-positive cell lines. This complex is referred to as ERF-1 (Estrogen Receptor Factor-1). Gel shift competitions were used to identify two ERF-1 binding sites within this 80 bp region. Cold competitor prepared from the entire 80 bp probe efficiently competes for binding. The region from +132 to +171 partially competes and +172 to +211 competes efficiently. Within the region from +172 to +211, the sequences from +182 to +211 compete efficiently for binding. Neither +172 to +191 nor +192 to +211 demonstrate any competition. ERF-1 binds to two sites in this region, a distal (high affinity) and a proximal (low affinity) site.

The distal binding site was mapped precisely utilizing gel shift competition with oligonucleotides containing mutations within the sequences from +182 to +201. This region contains the sequence CCCTGCGGGG (SEQ ID NO:01), which is an imperfect palindrome. The wild-type sequence of this distal site (dwt) competes efficiently. Mutations d1 nucleotides 190–191 (CC→AA) and nucleotides 195–196 (GG→AA) destroyed the ability of the oligonucleotide to compete, while mutations d2 nucleotides 185–186 (TC→AA) and d4 nucleotides 187–188 (TG→AA) do not alter the 10 bp imperfect palindrome and retain the ability to compete for binding although d4 is slightly less efficient than dwt. Mutation d5 nucleotide +192 (T→C) converting the sequence to a perfect palindrome partially weakens the ability to efficiently compete. The sequence between +132 to +171 that demonstrated weak competition was found to contain a second ERF-1 site located at +130 to +149, but in this region, a related sequence is found and homologous mutations as used for the distal site have identical consequences for binding. Insertion of a G between +140 and +141 creates a site identical to the distal site. This mutation improves the ability of the weak proximal site to compete.

Because the mutation p1 nucleotides 138–139 (CT→AA) destroys binding to the proximal site and d1 destroys binding to the distal site, these two mutations were built into the expression vector ER3500-230LUC and called ER3500-230p1d1. This new vector is identical to ERF3500-230LUC except for the two mutations within the proximal and distal ERF-1 binding sites. Mutation of these ERF-1 sites has an effect on expression similar to deletion of the region from +135 to +210. The results support the conclusion that ERF-1 is a transcription factor which is expressed in ER-positive breast carcinomas and which functions by binding to two sites in the untranslated leader of the ER gene.

A blot was reacted with a radiolabeled DNA probe from sequences +100 to +230 of the ER leader. This probe identified a 35 kD protein present in both MCF7 and MDA-MB-231 and a second protein of approximately 29–30 kD only found in MCF7. An identical blot was reacted with a probe prepared from a concatenated high-affinity distal ERF-1 binding site. This probe identified only the p29–30 protein found in MCF7 cells. These results indicate that the specific ERF-1 binding protein is a 29–30 kD protein expressed in MCF7 but not MDA-MB-231, or expressed in MD-MBA-231 in a form incapable of binding to the probe.

A panel of human cell lines was analyzed for ERF-1 expression using the gel shift assay, where abundant ERF-1 expression was found in ER-positive breast carcinoma cell lines tested—MCF7, T47D and BT20. Low levels of ERF-1 were detected in normal human mammary epithelial cells (HMEC). ERF-1 complex from HMEC demonstrate identical binding sequence specificity as a complex in MCF7 and T47D. HBL-100 is an ER-negative breast carcinoma line which appears to express low amounts of the ERF-1 comparable to HMEC. The only other cell line found to express abundant ERF-1 is RL95-2, which is an ER-positive human endometrial carcinoma (Way et al., In Vitro 19, 147 (1983)).

Purification of ERF-1

Buffers—The buffers used in the purification of ERF-1 contain the protease inhibitors pepstatin A, chymostatin, and antipain at a concentration of 1 µg/ml. Buffer H is 25 mM HEPES (pH 7.5)/5 mM KCl/1 mM $MgCl_2$/1 mM DTT/1 mM PMSF. Buffer E is 25 mM HEPES (pH 7.5)/10% sucrose/0.01% Nonidet P-40/1 mM DTT/1 mM PMSF. Buffer D is 25 mM HEPES (pH 7.5)/40% glycerol/0.01% Nonidet P-40/1 mM DTT/2 mM EDTA/0.1 mM PMSF. Buffer S is 25 mM HEPES (pH 7.5)/20% glycerol/0.01% Nonidet P-40/1 mM DTT/1 mM EDTA/0.1 mM PMSF.

Preparation of DNA-celluloses—DNA is adsorbed to cellulose according to the method of Alberts and Herrick (1971) Methods Enzymol. 21, 198–217, with the following modifications. The nonspecific DNA-cellulose is prepared from high molecular weight E. coli DNA (Miura, Methods Enzymol. 12A, 5543–555). The specific affinity matrix is prepared from DNA +135–+210 from the ER promoter region. DNA (1 mg/ml) is mixed with cellulose (0.5 g/ml DNA) and air-dried for 48 h followed by lyophilization for 12 h. The matrices are hydrated in Buffer S containing 2M NaCl and stored as a frozen slurry (−20° C.). The amount of DNA bound to cellulose (1 mg of DNA/ml of packed matrix) is estimated by $A_{260}$ measurements of the column effluent during the packing and equilibration steps.

Preparation of T47D Nuclear Extract—T47D cells are propagated at 37° C. in suspension culture in Eagle's minimal essential medium supplemented with 5% horse serum. Each liter of cells is grown to a density of 4–5×10$^5$ cells/ml and collected by centrifugation at 3000× g for 5 rain and washed twice with 15 ml of Buffer W. The washed cell pellets are frozen at −70° C. A total at 6×10$^{20}$ cells (120 g) are used in the purification. Each gram of T47D cells is thawed at 4° C. and resuspended in 5 ml of Buffer H containing 0.2% Nonidet P-40. Cells are completely disrupted by 10 strokes with a tight fitting dounce homogenizer and nuclei are collected by centrifugation at 1000× g for 5 min. The nuclear pellet is washed once with 5 ml of Buffer H containing 0.01% Nonidet P-40 and once with 5 ml of Buffer E. Nuclei are resuspended in 2.0 ml of Buffer E containing 0.35M NaCl and incubated on ice for 60 min. The residual nuclei are removed by centrifugation at 10,000× g for 30 min and an equal volume of Buffer D is added to the supernatant. T47D extract was loaded onto the high capacity cationic exchange resin Bio-Rex 70. This step removes about 88% of the loaded protein, significantly reducing the amount of DNA-cellulose matrix required for subsequent purification steps.

E. coli DNA-cellulose Chromatography—The diluted pool of activity from the Bio-Rex 70 column (430 ml, 550 mg) is loaded onto an E. coli DNA-cellulose column (60 ml, 2.5×12 cm) that has been pre-equilibrated with 200 mM NaCl in Buffer S. The matrix is washed with 200 mM NaCl in Buffer S (200 ml) and the DNA binding activity is eluted with a linear gradient from 200 to 500 mM NaCl in Buffer S (300 ml). The gradient elution is followed by a 2M NaCl step elution. The peak of specific DNA binding activity eluted in fractions between about 280 and 350 mM NaCl, which fractions are pooled (75 ml) and diluted with an equal volume of Buffer S.

T47D DNA-cellulose Chromatography—The diluted eluate from the E. coli DNA-cellulose column (62.5 mg, 75 ml) is loaded onto the specific DNA-cellulose column (5 ml, 1×6.3 cm) that has been pre-equilibrated with 200 mM NaCl in Buffer S. The column is washed with 200 mM NaCl in Buffer S (20 ml) and proteins are eluted with a linear gradient from 200 to 500 mM NaCl (30 ml). The specific DNA binding activity is recovered by screening fractions for binding to the specific sequence +172-+211. This eluate is diluted with 9 volumes of Buffer S and reapplied to the same T47D DNA-cellulose column that has been re-equilibrated with 200 mM NaCl in Buffer S. The column is washed with 0.2M NaCl (10 ml) followed by step elutions at 450 mM NaCl (20 ml) and 2M NaCl (20 ml). The specific DNA binding activity is isolated as indicated above. The eluate is dialyzed against 100 mM NaCl in Buffer S and is stored at −70° C.

Assay

Nitrocellulose Filter Binding Assay—The DNA used in the parallel nitrocellulose filter binding assays is +132-+211. The DNA is labeled at its 3' terminus ($4.0 \times 10^4$ cpm/fmol) by incubating with [$\alpha$-$^{32}$P]dATP and [$\alpha$-$^{32}$P]dTTP (3000 Ci/mmol) in the presence of *Micrococcus luteus* polymerase. Each assay (50 µl) contains 25 mM HEPES (pH 7.5)/150 mM NaCl/5 mM MgCl$_2$/1 mM DTT/2% glycerol/5 µg of BSA/5 µg of sheared *E. coli* DNA/0.1 nM $^{32}$P-DNA. Protein fractions are diluted (1:50–200) in Buffer S containing 25 mM NaCl and 5 µl of the dilution are added to a reaction mixture containing the specific DNA. The binding assays are incubated at 4° C. for 30 min and then filtered at a rate of 25 ml/h through nitrocellulose membrane mounted on a Schleicher and Schuell Minifold apparatus. Each sample is washed once with 0.5 ml of 25 mM HEPES (pH 7.5)/150 mM NaCl/2% glycerol/5 mM MgCl$_2$/1 mM DTT. Filters are dried and radioactive DNA bound to the filter is quantitated by liquid scintillation counting. Each assay is performed in duplicate and the average values are plotted.

The competition nitrocellulose filter binding assay is performed using a +132 to +211 dsDNA oligonucleotide sequence as previously described (Rawlins et al. (1984) Cell 37, 309–319) with the following modifications. Radioactive DNA is prepared as described previously for the standard nitrocellulose filter binding assays. The reaction mixtures contain 0.1 nM+132-+211 and plasmid pGL-2-Basic was used as competitor.

It is evident from the above results, that ERF-1 provides an opportunity to monitor the progress of ER-responsive carcinomas. In addition, one may also monitor the change in ERF-1 expression upon chemotherapy or other therapeutic treatment. Also, ERF-1 provides a target which can be used for screening drugs which will bind to ERF-1 and inhibit expression of the estrogen receptor. In this manner, one may reduce the proliferative and aggressive phenotype of mammary tumors.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for determining the cellular level of estrogen receptor factor–1 (ERF-1) in a mammalian host cell, said method comprising:
   combining a cellular lysate or portion thereof with an agent which specifically binds to ERF-1 to form a binding pair complex of said agent and said ERF-1; and
   detecting the presence of said binding pair complex as indicative of the presence of ERF- 1.

2. A method according to claim 1, wherein said mammalian host cell is a mammary or endometrial tumor cell.

3. A method according to claim 1, wherein said host cell is estrogen dependent for proliferation.

4. A method for determining the cellular level of estrogen receptor factor–1 (ERF-1) in a human mammary or endometrial tumor cell, said method comprising:
   combining a cellular lysate or portion thereof with a labeled dsDNA molecule which specifically binds to ERF-1 to form a binding pair complex of said labeled dsDNA molecule and ERF-1; and
   detecting the presence of said binding pair complex as indicative of the presence of ERF-1.

5. A method according to claim 4, wherein said labeled dsDNA molecule comprises CCCTGCGGGG (SEQ ID NO:01 ).

6. A method according to claim 4, wherein said detecting comprises separating said binding pair complex from other components of said lysate by means of gel electrophoresis.

7. A method for determining the cellular level of estrogen receptor factor–1 (ERF-1) in a human mammary or endometrial tumor cell, said method comprising:

combining a cellular lysate or portion thereof with a labeled dsDNA molecule comprising CCCTGCGGGG (SEQ ID NO:01) to form a binding pair complex of said dsDNA molecule and ERF-1;

separating said binding pair complex from other components of said lysate by means of gel electrophoresis; and detecting said binding pair complex as indicative of the presence of ERF-1.

8. A method according to claim 7, wherein said labeled dsDNA molecule comprises a radioisotope.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:1:

CCCTGCGGGG    10